United States Patent
Pigott

(10) Patent No.: US 10,939,936 B2
(45) Date of Patent: *Mar. 9, 2021

(54) INTRAVASCULAR CATHETER WITH INCISING DEVICES

(71) Applicant: John P. Pigott, Sylvania, OH (US)

(72) Inventor: John P. Pigott, Sylvania, OH (US)

(73) Assignee: VENTUREMED GROUP, INC., Plymouth, MN (US)

( * ) Notice: Subject to any disclaimer, the term of this patent is extended or adjusted under 35 U.S.C. 154(b) by 527 days.

This patent is subject to a terminal disclaimer.

(21) Appl. No.: 15/861,955

(22) Filed: Jan. 4, 2018

(65) Prior Publication Data

US 2018/0125525 A1  May 10, 2018

Related U.S. Application Data

(63) Continuation of application No. 15/481,552, filed on Apr. 7, 2017, now Pat. No. 10,485,572, which is a
(Continued)

(51) Int. Cl.
*A61B 17/3207* (2006.01)
*A61B 17/3209* (2006.01)
*A61B 17/00* (2006.01)

(52) U.S. Cl.
CPC .. *A61B 17/320725* (2013.01); *A61B 17/3209* (2013.01); *A61B 17/32075* (2013.01); *A61B 2017/00986* (2013.01)

(58) Field of Classification Search
CPC ........ A61B 17/320783; A61B 17/3209; A61B 17/320725; A61B 17/320708;
(Continued)

(56) References Cited

U.S. PATENT DOCUMENTS 2,655,154 A   11/1951   Richter
3,557,794 A   1/1971   Van Patten
(Continued)

FOREIGN PATENT DOCUMENTS

EP   0727194 A1   8/1996
WO   8102109 A1   8/1981
(Continued)

OTHER PUBLICATIONS

Cardiovascular Systems Inc., Diamondback 360 Coronary Orbital Atherectomy System, http://www.csi360.com/products/coronary-diamondback-360-coronary-orbital-atherectomy-system-crowns/, 2016.
(Continued)

*Primary Examiner* — Tan-Uyen T Ho
*Assistant Examiner* — Chima U Igboko
(74) *Attorney, Agent, or Firm* — Standley Law Group LLP; Adam J. Smith

(57) ABSTRACT

An intravascular device is provided having a flexible catheter tube with an expandable portion located on an end thereof. The expandable portion has a plurality of struts capable of being moved between an expanded and a collapsed position. An incising element provided along at least a portion of one of the struts has a sharpened edge for creating an incision in atherosclerotic material located within a blood vessel and generating microparticles of the same when the expandable portion is in the expanded position.

20 Claims, 6 Drawing Sheets

Related U.S. Application Data continuation of application No. 13/613,914, filed on Sep. 13, 2012, now Pat. No. 9,615,848.

(60) Provisional application No. 61/534,018, filed on Sep. 13, 2011.

(58) Field of Classification Search
CPC ........ A61B 17/3207; A61B 17/320758; A61B 17/3439; A61B 17/320016; A61B 17/32002; A61B 2017/00986; A61B 2017/320741; A61B 2017/320766; A61B 2017/320755; A61B 2017/320791; A61B 2017/320024; A61B 2017/320028; A61B 2017/320032; A61B 5/6858
See application file for complete search history.

(56) References Cited

U.S. PATENT DOCUMENTS

| | | |
|---|---|---|
| 3,704,711 A | 12/1972 | Park |
| 4,273,128 A | 6/1981 | Banning |
| 4,292,974 A | 10/1981 | Fogarty et al. |
| 4,654,027 A | 3/1987 | Dragan et al. |
| 5,030,201 A | 7/1991 | Palestrant |
| 5,074,871 A | 12/1991 | Groshong |
| 5,100,425 A | 3/1992 | Fischell et al. |
| 5,154,724 A | 10/1992 | Andrews |
| 5,156,610 A | 10/1992 | Reger |
| 5,178,625 A | 1/1993 | Groshong |
| 5,211,651 A | 5/1993 | Reger et al. |
| 5,224,945 A | 7/1993 | Pannek, Jr. |
| 5,244,619 A | 9/1993 | Burnham |
| 5,246,421 A | 9/1993 | Saab |
| 5,250,060 A | 10/1993 | Carbo et al. |
| 5,282,484 A | 2/1994 | Reger |
| 5,312,427 A | 5/1994 | Shturman |
| 5,318,576 A | 6/1994 | Plassche, Jr. et al. |
| 5,514,093 A | 5/1996 | Ellis et al. |
| 5,591,194 A | 1/1997 | Berthiaume |
| 5,658,309 A | 8/1997 | Berthiaume et al. |
| 5,665,098 A | 9/1997 | Kelly et al. |
| 5,676,654 A | 10/1997 | Ellis et al. |
| 5,697,944 A | 12/1997 | Lary |
| 5,697,948 A | 12/1997 | Marin et al. |
| 5,728,067 A | 3/1998 | Enger |
| 5,728,123 A | 3/1998 | Lemelson et al. |
| 5,733,296 A | 3/1998 | Rogers et al. |
| 5,792,158 A | 8/1998 | Lary |
| 5,800,450 A | 9/1998 | Lary et al. |
| 5,836,868 A | 11/1998 | Ressemann et al. |
| 5,876,448 A | 3/1999 | Thompson et al. |
| 5,961,536 A | 10/1999 | Mickley et al. |
| 5,968,064 A | 10/1999 | Selmon et al. |
| 6,071,287 A | 6/2000 | Verbeek |
| 6,120,515 A | 9/2000 | Rogers et al. |
| 6,129,708 A | 10/2000 | Enger |
| 6,165,187 A | 12/2000 | Reger |
| 6,217,549 B1 | 4/2001 | Selmon et al. |
| 6,258,108 B1 | 7/2001 | Lary |
| 6,270,489 B1 | 8/2001 | Wise et al. |
| 6,283,947 B1 | 9/2001 | Mirzaee |
| 6,527,740 B1 | 3/2003 | Jackson et al. |
| 6,599,267 B1 | 7/2003 | Ray et al. |
| 6,692,466 B1 | 2/2004 | Chow et al. |
| 6,695,863 B1 | 2/2004 | Ramzipoor et al. |
| 6,719,773 B1 | 4/2004 | Boucher et al. |
| 6,884,257 B1 | 4/2005 | Cox |
| 7,108,704 B2 | 9/2006 | Trerotola |
| 7,131,981 B2 | 11/2006 | Appling et al. |
| 7,279,002 B2 | 10/2007 | Shaw et al. |
| 7,303,572 B2 | 12/2007 | Melsheimer et al. |
| 7,329,267 B2 | 2/2008 | Weber |
| 7,517,352 B2 | 4/2009 | Evans et al. |
| 7,686,824 B2 | 3/2010 | Konstantino et al. |
| 7,691,086 B2 | 4/2010 | Tkebuchava |
| 7,708,753 B2 | 5/2010 | Hardert |
| 7,850,685 B2 | 12/2010 | Kunis et al. |
| 7,850,710 B2 | 12/2010 | Huss |
| 7,887,557 B2 | 2/2011 | Kelley et al. |
| 7,955,350 B2 | 6/2011 | Konstantino et al. |
| 8,323,307 B2 | 12/2012 | Hardert |
| 8,328,829 B2 | 12/2012 | Olson |
| 8,348,987 B2 | 1/2013 | Eaton |
| 8,366,661 B2 | 2/2013 | Weber et al. |
| 8,398,662 B2 | 3/2013 | Granada et al. |
| 8,454,636 B2 | 6/2013 | Konstantino et al. |
| 8,500,789 B2 | 8/2013 | Wuebbeling et al. |
| 8,685,049 B2 | 4/2014 | Schur et al. |
| 8,685,050 B2 | 4/2014 | Schur et al. |
| 8,702,736 B2 | 4/2014 | Schur et al. |
| 8,740,849 B1 | 6/2014 | Fischell et al. |
| 8,870,816 B2 | 10/2014 | Chambers et al. |
| 9,079,000 B2 | 7/2015 | Hanson et al. |
| 9,192,747 B2 | 11/2015 | Hardert |
| 9,282,991 B2 | 3/2016 | Schur et al. |
| 9,364,255 B2 | 6/2016 | Weber |
| 9,364,284 B2 | 6/2016 | Groff et al. |
| 9,510,901 B2 | 12/2016 | Steinke et al. |
| 9,532,798 B2 | 1/2017 | Schur et al. |
| 9,592,386 B2 | 3/2017 | Mathur et al. |
| 9,604,036 B2 | 3/2017 | Burton et al. |
| 9,615,848 B2 * | 4/2017 | Pigott ............ A61B 17/320725 |
| 10,485,572 B2 * | 11/2019 | Pigott ................ A61B 17/3209 |
| 10,610,255 B2 * | 4/2020 | Pigott ............... A61M 25/0074 |
| 2001/0007059 A1 | 7/2001 | Mirzaee |
| 2002/0010489 A1 | 1/2002 | Grayzel et al. |
| 2002/0143350 A1 | 10/2002 | Heitzmann et al. |
| 2003/0069547 A1 | 4/2003 | Gonon |
| 2003/0125756 A1 | 7/2003 | Shturman et al. |
| 2003/0144677 A1 | 7/2003 | Lary |
| 2004/0034384 A1 | 2/2004 | Fukaya |
| 2004/0098014 A1 | 5/2004 | Flugelman |
| 2004/0122457 A1 | 6/2004 | Weber |
| 2004/0204738 A1 | 10/2004 | Weber et al. |
| 2004/0267345 A1 | 12/2004 | Lorenzo et al. |
| 2005/0055077 A1 | 3/2005 | Marco et al. |
| 2005/0149102 A1 | 7/2005 | Radisch, Jr. et al. |
| 2005/0149159 A1 | 7/2005 | Andreas et al. |
| 2005/0151304 A1 | 7/2005 | Boelens et al. |
| 2005/0240176 A1 | 10/2005 | Oral et al. |
| 2006/0089637 A1 | 4/2006 | Werneth et al. |
| 2006/0111736 A1 | 5/2006 | Kelley |
| 2006/0116701 A1 | 6/2006 | Crow |
| 2006/0184191 A1 | 8/2006 | O'Brien |
| 2007/0005093 A1 | 1/2007 | Cox |
| 2007/0060863 A1 | 3/2007 | Goeken et al. |
| 2007/0106215 A1 | 5/2007 | Olsen et al. |
| 2007/0156225 A1 | 7/2007 | George et al. |
| 2007/0181157 A1 | 8/2007 | Dadourian |
| 2007/0238960 A1 | 10/2007 | Thorn |
| 2008/0140051 A1 | 6/2008 | Bei et al. |
| 2008/0294116 A1 | 11/2008 | Wolter et al. |
| 2008/0300594 A1 | 12/2008 | Goto |
| 2008/0300610 A1 | 12/2008 | Chambers |
| 2009/0099583 A1 | 4/2009 | Butterfield et al. |
| 2009/0105686 A1 | 4/2009 | Snow et al. |
| 2009/0192508 A1 | 7/2009 | Laufer et al. |
| 2009/0204068 A1 | 8/2009 | Nguyen et al. |
| 2009/0306690 A1 | 12/2009 | Rivers et al. |
| 2009/0312807 A1 | 12/2009 | Boudreault et al. |
| 2010/0010521 A1 | 1/2010 | Kurrus |
| 2010/0023035 A1 | 1/2010 | Kontos |
| 2010/0121270 A1 | 5/2010 | Gunday et al. |
| 2010/0168737 A1 | 7/2010 | Grunewald |
| 2010/0168778 A1 | 7/2010 | Braido |
| 2010/0330147 A1 | 12/2010 | Hossainy et al. |
| 2011/0060182 A1 | 3/2011 | Kassab et al. |
| 2011/0152683 A1 | 6/2011 | Gerrans et al. |
| 2011/0160645 A1 | 6/2011 | Sutermeister et al. |
| 2011/0184447 A1 | 7/2011 | Leibowitz et al. |
| 2011/0288479 A1 | 11/2011 | Burton |
| 2012/0053485 A1 | 3/2012 | Bloom |
| 2012/0143054 A1 | 6/2012 | Eaton et al. |

(56) References Cited

U.S. PATENT DOCUMENTS

| | | |
|---|---|---|
| 2012/0157988 A1 | 6/2012 | Stone et al. |
| 2012/0172901 A1 | 7/2012 | Manderfeld et al. |
| 2013/0066346 A1* | 3/2013 | Pigott ............ A61B 17/320725 606/159 |
| 2013/0131594 A1 | 5/2013 | Bonnette et al. |
| 2013/0150874 A1 | 6/2013 | Kassab |
| 2013/0237950 A1 | 9/2013 | Gianotti et al. |
| 2013/0253467 A1 | 9/2013 | Gianotti et al. |
| 2014/0277002 A1 | 9/2014 | Grace |
| 2014/0364896 A1 | 12/2014 | Consigny |
| 2015/0133978 A1 | 5/2015 | Paul, Jr. |
| 2017/0056048 A1 | 3/2017 | Erpen |
| 2017/0238960 A1 | 8/2017 | Hatta et al. |

FOREIGN PATENT DOCUMENTS

| | | |
|---|---|---|
| WO | 9502370 A2 | 1/1995 |
| WO | 1996039997 A2 | 12/1996 |
| WO | 9918862 A1 | 4/1999 |
| WO | 02078511 A2 | 10/2002 |
| WO | 02078511 A3 | 10/2002 |
| WO | 2007095125 A2 | 8/2007 |
| WO | 2013159066 A1 | 10/2013 |
| WO | 2014106226 A2 | 7/2014 |
| WO | 2014142801 A1 | 9/2014 |
| WO | 2015195606 A1 | 12/2015 |
| WO | WO2015190578 A1 | 12/2015 |
| WO | 2016210167 A1 | 12/2016 |

OTHER PUBLICATIONS

Boston Scientific, Rotablator Rotational Atherectomy System, http://www.bostonscientific.com/en-US/products/plaque-modification/rotablator-rotational-atherectomy-system.html, 2017.
International Search Report, Application No. PCT/US2012/055079, dated Jan. 31, 2013.
Boston Scientific Corporation, FilterWire EZ, Embolic Protection System for Carotid Arteries, Sep. 2015, http://www.bostonscientific.com/en-US/products/embolic-protection/filterwire-ez-embolic-protection-system.html.
Covidien, SpiderFX Embolic Protection Device, 2015, https://www.ev3.net/peripheral/us/embolic-protection/spiderfxtrade-embolic-protection-device.htm.
Boston Scientific, Sterling 0.018" Balloon Catheter, Jun. 2015.
Ham, S. et al., Safety of Carbon Dioxide Digital Subtraction Angiography, Archives of Surgery, Dec. 2011.
Alexander, J., CO2 Angiography in Lower Extremity Arterial Disease, Endovascular Today, Sep. 2011, pp. 27-34.

* cited by examiner

INTRAVASCULAR CATHETER WITH INCISING DEVICES

CROSS-REFERENCE TO RELATED APPLICATIONS

This application is a continuation of application Ser. No. 15/481,552, which is a continuation of application Ser. No. 13/613,914, filed Sep. 13, 2012 and now issued as U.S. Pat. No. 9,615,848 dated Apr. 11, 2017, which claims the benefit of U.S. Provisional Application No. 61/534,018, filed Sep. 13, 2011, the disclosures of all of which are hereby incorporated by reference in their entirety.

BACKGROUND OF THE INVENTION

This invention relates in general to intravascular catheters, such as can be used during minimally invasive surgical procedures. In particular, this invention relates to an intravascular catheter having an expandable incising portion.

Atherosclerosis is a chronic condition in which atheromatous plaque accumulates on the inner walls of a blood vessel. As a result, the blood vessel walls can become inflamed and, over time, may harden to form atherosclerotic lesions that cause a narrowing of the vessel lumen. In severe cases, the atherosclerotic lesions can rupture and induce the formation of thrombus (i.e., blood clots), which can prevent blood flow through the narrowed vessel lumen.

There are known procedures and devices for treating or otherwise reducing the risks associated with atherosclerosis. For example, an angioplasty is a procedure in which a balloon catheter is inserted into a narrowed region of the vessel lumen via a delivery catheter. The balloon catheter includes a flexible tube having an inflatable balloon at an end thereof. Once positioned in the narrowed region, the balloon is inflated in order to dilate the narrowed vessel lumen. The pressure in the balloon is generally sufficient to compress the accumulated plaque. However, in some cases it would be desirable to fragment the atherosclerotic lesions. Thus, it would be desirable to provide an intravascular catheter having an expandable portion that can be selectively controlled by a user and adapted to create incisions in atherosclerotic material to facilitate fragmentation of the material during an angioplasty procedure.

SUMMARY OF THE INVENTION

This invention relates to an intravascular catheter device for use during a surgical procedure. The catheter device includes a catheter tube having an expandable portion with a plurality of struts each defining an outer surface. The expandable portion is operable between a closed position, wherein the expandable portion has a first diameter, and an opened position, wherein the expandable portion has a second diameter that is larger than the first diameter. An incising element is provided on the outer surface of at least one of the struts. The incising element has a sharpened edge that extends outwardly in a radial direction from the outer surface of the strut for creating an incision in atherosclerotic material located within a blood vessel when the expandable portion is in the opened position.

Various aspects of this invention will become apparent to those skilled in the art from the following detailed description of the preferred embodiments, when read in light of the accompanying drawings.

DETAILED DESCRIPTION OF THE PREFERRED EMBODIMENTS

Figure 1:
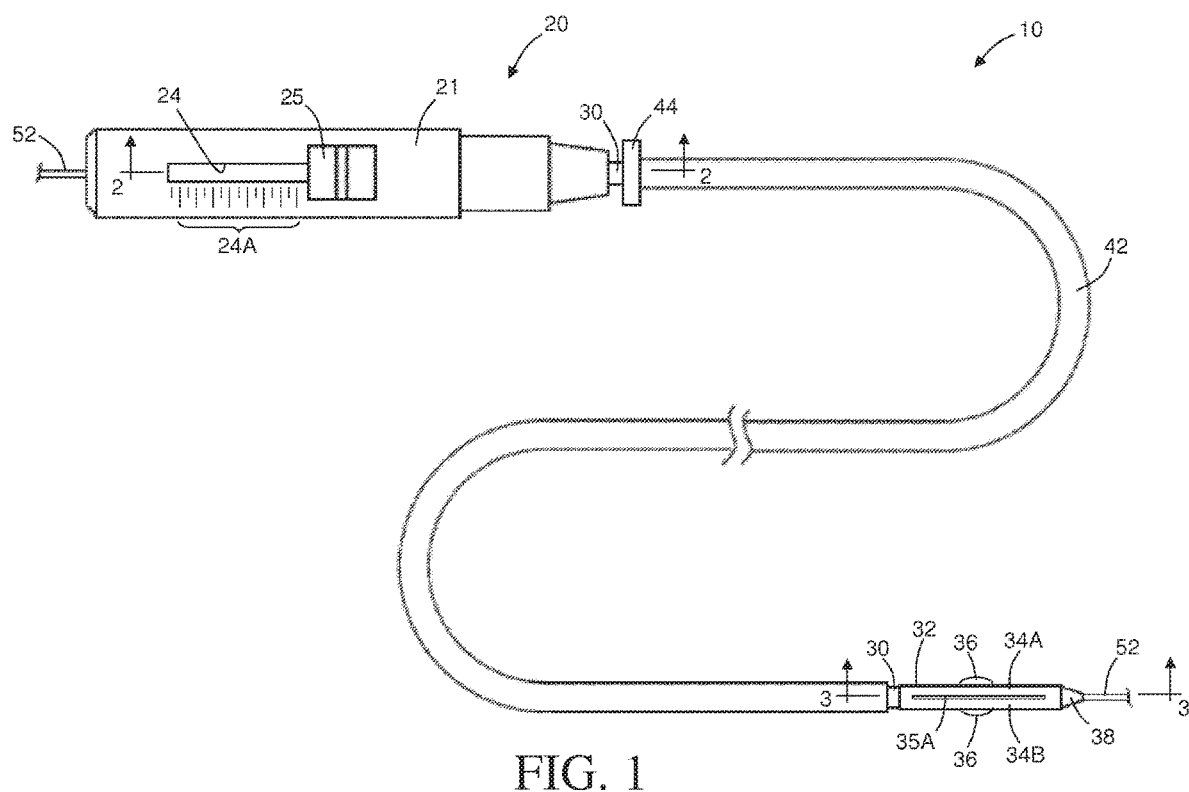
FIG. 1 is a plan view of a catheter device that includes a handle assembly and a catheter tube having an expandable incising portion, in accordance with a first embodiment of this invention.

Referring now to the drawings, there is illustrated in FIG. 1 a catheter device, indicated generally at 10, in accordance with this invention. The illustrated catheter device 10 is configured to treat or reduce the risks associated with atherosclerosis. In general, the catheter device 10 includes an expandable incising portion that can be inserted into a blood vessel and expanded to create incisions in atherosclerotic material that has accumulated on inner walls of the blood vessel. The incisions facilitate the fragmentation of the atherosclerotic material during a subsequent angioplasty or atherectomy procedure. Although the catheter device 10 will be described and illustrated in the context of treating atherosclerosis, it should be appreciated that the catheter device 10 can be used in any desired environment and for any desired purpose.

Figure 2:
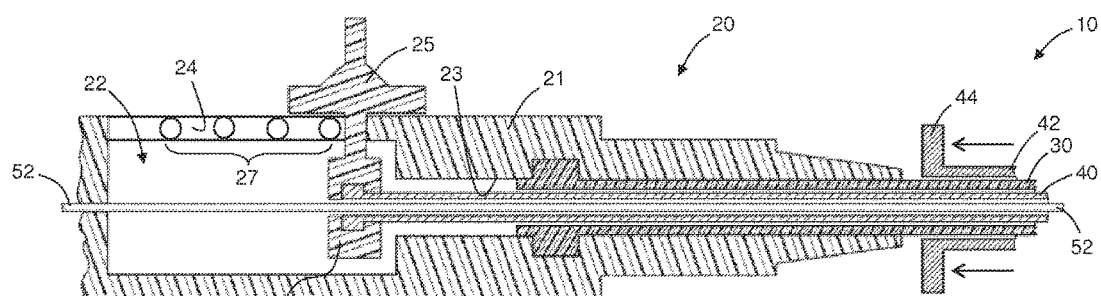
FIG. 2 is a cross-sectional side view of the handle assembly taken along section line 2-2 shown in FIG. 1 when the catheter device is in a first operating mode.

Referring now to FIGS. 1 and 2, the illustrated catheter device 10 includes a handle assembly, indicated generally at 20. The illustrated handle assembly 20 includes an elongated, cylindrical handle body 21. The handle body 21 may alternatively have any other shape that is suitable for easy handling by a surgeon. Further, the handle body 21 can be made from any suitably rigid material including, but not limited to, stainless steel or polymers.

As shown in FIG. 2, the illustrated handle body 21 defines an internal chamber 22. A passage 23 extends into an end portion of the handle body 21 for communication with the internal chamber 22. The handle body 21 further includes a slot 24 that extends through a side wall thereof for communication with the internal chamber 22. The illustrated slot 24 may have any length or width as desired. As shown in FIG. 1, an indicator 24A may be provided on the handle body 21 adjacent to the slot 24. For example, the indicator 24A can be a visual scale or any other indicating means, the purpose of which will be explained below.

The illustrated handle assembly 20 also includes a control member 25 that is supported on the handle body 21 for sliding movement within the slot 24. For example, the control member 25 is movable between a forward position (shown in FIG. 2), a rearward position (shown in FIG. 5), or any position therebetween, which will be further explained below. As shown in FIG. 2, the illustrated control member 25 includes a base portion 26 that is disposed within the internal chamber 22 of the handle body 21. The base portion 26 may define an outer cross-sectional shape that generally corresponds with a cross-sectional shape of the internal chamber 22, although such is not required. Alternatively (or in addition), the control member 25 may be movably supported on the handle body 21 by a bearing, a bushing, a guide rail, or any other structural means. In other embodiments, the control member 25 may be supported for rotational movement, pivotal movement, or any other type of movement relative to the handle body 21, the purpose of which will become apparent below. The visual indicator 24A, described above, is configured to identify the relative position of the control member 25 with respect to the handle body 21.

The illustrated handle assembly 20 also includes a locking mechanism 27 that is configured to temporarily secure the control member 25 in a desired position, although such is not required. As shown in FIG. 2, the illustrated locking mechanism 27 includes a plurality of protrusions that are spaced apart from one another along an inner surface of the slot 24. The control member 25 frictionally engages the protrusions to hold the control member 25 in the desired position. Alternatively, the locking mechanism 27 may be a threaded fastener, a pivotal latch, a push-button release, or any other mechanism that is configured to secure the control member 25 in a desired position.

Figure 3:
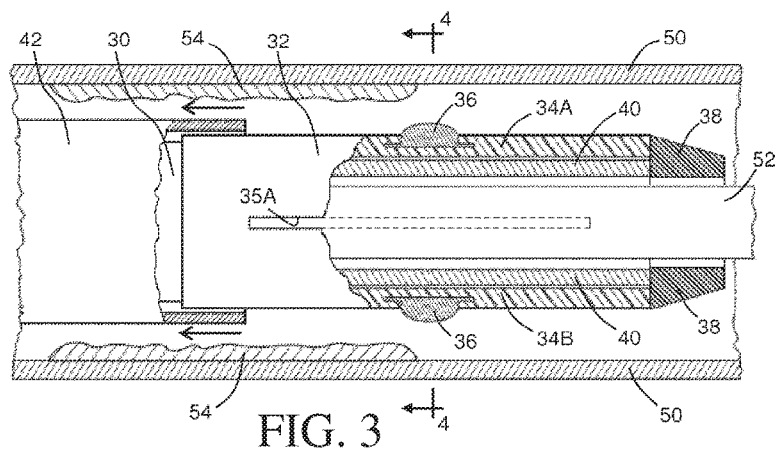
FIG. 3 is an enlarged cross-sectional side view of the catheter tube taken along section line 3-3 shown in FIG. 1 illustrating the expandable incising portion disposed within a blood vessel.

Referring now to FIGS. 1 through 3, the illustrated catheter device 10 also includes a catheter tube 30 that extends from the handle assembly 20. The catheter tube 30 is an elongated, flexible member having a proximal end that is secured to the handle assembly 20 and a distal end that extends therefrom. The catheter tube 30 can be made from any biocompatible material including, but not limited to, polyvinyl, polyethylene, nitinol, or stainless steel. Further, the catheter tube 30 can have any outer diameter, length, or wall thickness.

As shown in FIG. 2, the proximal end of the catheter tube 30 is secured to the handle body 21 and communicates with the internal cavity 22 through the passage 23. The catheter tube 30 may be secured to the handle body 21 using a flanged connection, a fused connection, an adhesive, a press-fit connection, a threaded connection, or any other securing means. Alternatively, the catheter tube 30 may be secured to the handle body 21 using a connector or any other type of attachment device.

As shown in FIGS. 1 and 3, an expandable portion 32 is provided on the distal end of the catheter tube 30. The illustrated expandable portion 32 is a cylindrical member having a longitudinal axis. The expandable portion 32 can be made from a generally resilient material that is able to flex between various positions, such as polyvinyl, polyethylene, nitinol, or stainless steel. The expandable portion 32 can be secured to the catheter tube 30 in any manner including, but not limited to, a fused connection, an adhesive, a press-fit connection, a threaded connection, or any other securing means. Alternatively, the expandable portion 32 can be integrally formed from the catheter tube 30. Further, the expandable portion 32 can have any outer diameter, length, or wall thickness.

Figure 4:
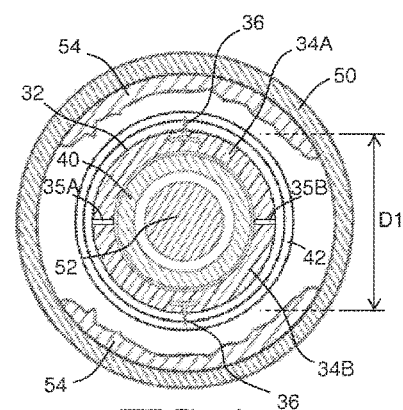
FIG. 4 is a cross-sectional end view of the expandable incising portion taken along section line 4-4 shown in FIG. 3.

The illustrated expandable portion 32 has a pair of struts 34A and 34B. The illustrated struts 34A and 34B are separated by a pair of longitudinally extending slits 35A and 35B that extend through side walls of the expandable portion 32. As shown in FIG. 4, the slits 35A and 35B are equally spaced apart from one another around the circumference of the expandable portion 32 such that the struts 34A and 34B have the same circumferential widths, although such is not required. The struts 34A and 34B may have any length, circumferential width, or cross-sectional shape as desired.

As shown in FIGS. 3 and 4, the illustrated expandable portion 32 also includes a pair of incising elements 36 that are respectively provided along outer surfaces of the struts 34A and 34B. The incising elements 36 can be atherotomes or other incising members having arcuate shaped sharpened edges, for example, that are configured to create incisions in atherosclerotic material as will be explained below. The illustrated incising elements 36 extend parallel with the longitudinal axis of the expandable portion 32 and outwardly in a radial direction therefrom. The incising elements 36 are equally spaced apart from one another around the circumference of the expandable portion 32. The expandable portion 32 may, however, have any number or configuration of incising elements 36 provided around the circumference thereof. Further, the incising elements 36 can have any cross-sectional shape, longitudinal length, or height and can be made from any suitable material including, but not limited to, tempered steel, stainless steel, high carbon steel, or ceramics. The incising elements 36 can be molded with the struts 34A and 34B or may otherwise be secured thereto in any manner such as, for example, using a welded or soldered connection, an adhesive, or any other fastening means.

The distal end of the expandable portion 32 may optionally include a tip member 38. The illustrated tip member 38 has a generally conical shape that facilitates insertion of the catheter tube 30 within a blood vessel 50 (see FIGS. 3 and 4) and subsequent travel therethrough. The tip member 38 may, however, have any desired shape. An aperture may axially extend through the tip member 38, the purpose of which will be explained below. The tip member 38 can be integrally formed with the expandable portion 32 or may be secured thereto, such as with an adhesive or the like. Further, the tip member 38 can be made from any biocompatible material including, but not limited to, polyvinyl, polyethylene, nitinol, stainless steel, or polyether block amide.

As shown in FIGS. 2 through 4, the illustrated catheter device 10 also includes an inner sleeve 40, although such is not required. The inner sleeve 40 is a flexible, tubular member that is supported for sliding movement within the catheter tube 30, the purpose of which will be explained below. The inner sleeve 40 can be made from any biocompatible material including, but not limited to, polyvinyl, polyethylene, nitinol, stainless steel, or a woven material. Further, the inner sleeve 40 can have any outer diameter, length, or wall thickness. The inner sleeve 40 need not be a tubular member but may alternatively be a solid wire, a braided wire, or the like.

As shown in FIG. 2, a proximal end of the inner sleeve 40 extends from the catheter tube 30 and into the internal chamber 22 of the handle body 21. The proximal end of the inner sleeve 40 is secured to the base portion 26 of the control member 25 for sliding movement therewith, the purpose of which will be explained below. The inner sleeve 40 can be secured to the base portion 26 by a flanged connection, a fused connection, an adhesive, a threaded connection, or any other securing means.

As shown in FIG. 3, the inner sleeve 40 extends through an entire length of the catheter tube 30. A distal end of the inner sleeve 40 that is opposite the handle assembly 20 is secured to the tip member 38, which is in turn secured to the expandable portion 32. The inner sleeve 40 may be secured to the tip member 38 in any manner including, but not limited to, a fused connection, an adhesive, a fastener, or the like.

Referring back to FIGS. 1 and 2, the illustrated catheter device 10 also includes a protective sheath 42 that is supported for sliding movement along an outer surface of the catheter tube 30, although such is not required. The protective sheath 42 can be made from any biocompatible material including, but not limited to, polyvinyl, polyethylene, nitinol, or stainless steel. Further, the protective sheath 42 can have any outer diameter, length, or wall thickness. The purpose of the protective sheath 42 will be explained below.

The illustrated protective sheath 42 includes a flange 44 that facilitates sliding movement of the protective sheath 42 relative to the catheter tube 30. The illustrated flange 44 is an annular member that is located at an end of the protective sheath 42 nearest the handle assembly 20. The flange 44 can be integrally formed with the protective sheath 42 or may otherwise be secured thereto in any manner, such as with an adhesive or the like. It should be appreciated that the flange 44 can have any shape or may alternatively be configured in any manner to accomplish the functions described herein and below.

The operation of the catheter device 10 will now be described with reference to FIGS. 1 through 7. Referring initially to FIGS. 1 through 4, the catheter device 10 is illustrated in a first operating mode. In the first operating mode, the control member 25 on the handle assembly 20 is located in the forward position relative to the handle body 21. The inner sleeve 40 fully extends into the catheter tube 30 such that the expandable portion 32 is in a closed position, as shown in FIGS. 3 and 4. In the closed position, the struts 34A and 34B are generally parallel with one another and with the inner sleeve 40. The slits 35A and 35B (illustrated by the dashed lines in FIG. 3) remain in a generally closed configuration. As such, the expandable portion 32 defines an initial diameter D1, which is generally the same diameter as the remaining length of the catheter tube 30. The initial diameter D1 of the expandable portion 32 may, however, be any desired dimension.

When the catheter device 10 is in the first operating mode, the distal end of the catheter tube 30 can be percutaneously inserted into a blood vessel 50, as shown in FIGS. 3 and 4. The illustrated catheter tube 30 is then advanced through the blood vessel 50 along a guide wire 52, which extends through the catheter device 10. For example, the guide wire 52 may fully extend through the inner sleeve 40, into the internal chamber 22 of the handle body 21, and exit a rear end of the handle assembly 20 (see FIG. 2). The catheter tube 30 is advanced along the guide wire 52 until the expandable portion 32 is positioned in a narrowed region of the blood vessel 50 caused by atherosclerotic material 54. Alternatively, the catheter tube 30 can be inserted into the blood vessel 50 and guided therethrough by a delivery catheter (not shown) or any other suitable procedure. During insertion and advancement of the catheter tube 30 through the blood vessel 50, the optional protective sheath 42 is preferably positioned over the expandable portion 32, thereby preventing the incising elements 36 from coming into contact with inner walls of the blood vessel 50.

Once the expandable portion 32 is positioned in the narrowed region of the blood vessel 50, the incising elements 36 can be exposed by sliding the protective sheath 42 back from the distal end of the catheter tube 30, as indicated by the direction arrows in FIG. 3. The illustrated protective sheath 42 can be moved in this manner by pulling the flange 44 towards the handle assembly 20, which is indicated by the direction arrows in FIG. 2.

Figure 5:
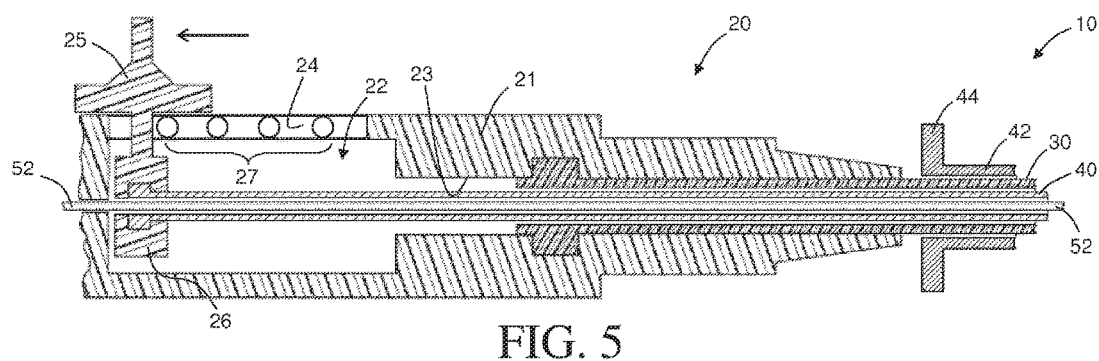
FIG. 5 is a cross-sectional side view of the handle assembly taken along section line 2-2 shown in FIG. 1 when the catheter device is in a second operating mode.
Figure 6:
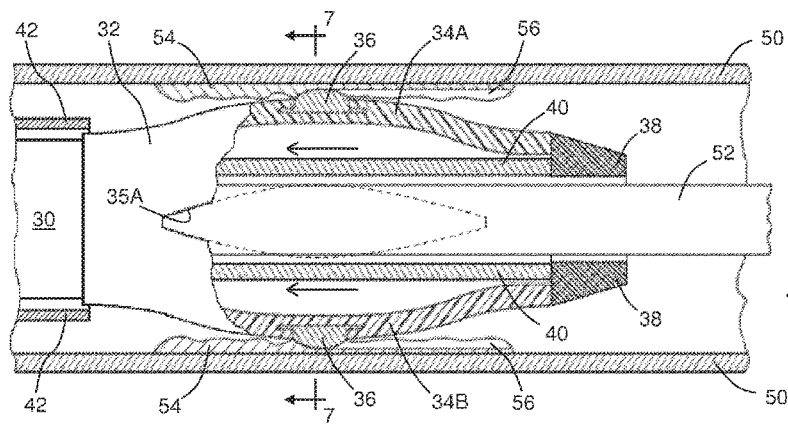
FIG. 6 is an enlarged cross-sectional side view of the catheter tube taken along section line 3-3 shown in FIG. 1 illustrating the expandable incising portion in an opened position.
Figure 7:
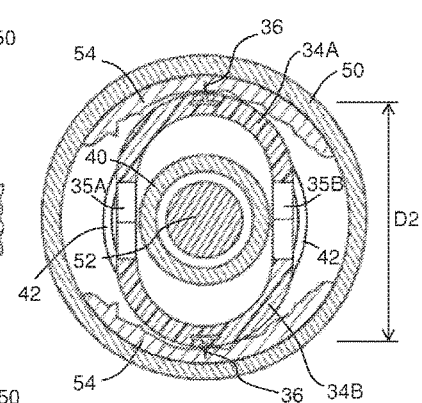
FIG. 7 is a cross-sectional end view of the expandable incising portion taken along section line 7-7 shown in FIG. 6.

Referring now to FIGS. 5 through 7, the catheter device 10 is illustrated in a second operating mode. To achieve the second operating mode, the control member 25 is moved from the forward position to the rearward position, as indicated by the direction arrow in FIG. 5. As the control member 25 is moved to the rearward position, the inner sleeve 40 is drawn within the catheter tube 30 thereby reducing the relative length of the inner sleeve 40 with respect to the catheter tube 30. The distal end of the inner sleeve 40 is attached to the tip member 38, as described above, causing the expandable portion 32 to become axially compressed between the tip member 38 and the distal end of the catheter tube 30. As a result, the struts 34A and 34B bow or expand outwardly in a generally arcuate fashion thereby defining an opened position. In the opened position, the expandable portion 32 defines a second diameter D2 that is larger than the initial diameter D1 when the expandable portion 32 is in the closed position. As shown in FIG. 6, the incising elements 36 are respectively positioned along the radially outer most surfaces of the struts 34A and 34B. Further, the outer most surfaces of the struts 34A and 34B may define a generally flat portion along a length thereof in the opened position, the purpose of which will be explained below, although such is not required. It should be appreciated that the struts 34A and 34B can have any lengths such that the expandable portion 32 can achieve a desired overall second diameter D2 in the opened position.

During operation of the catheter device 10, the second diameter D2 can be increased or decreased by selective movement of the control member 25 between the forward and rearward positions. For example, a larger second diameter D2 can be achieved by moving the control member 25 further towards the rearward position. Conversely, a smaller second diameter D2 can be achieved by moving the control member 25 further towards the forward position. The visual indicator 24A can be used to identify the instantaneous second diameter D2 of the expandable portion 32. Alternatively (or in addition), the struts 34A and 34B may be biased in the opened position so as to automatically expand outwardly to the second diameter D2 when the protective sheath 42 is slid back from the expandable portion 32. As such, sliding movement of the protective sheath 42 relative to the struts 34A and 34B can be used to selectively control the second diameter D2. In this configuration, the inner sleeve 40 and the movable components of the handle assembly 20 may not be necessary.

When the catheter device 10 is in the second operating mode, the expandable portion 32 can be pulled along the guide wire 52 through the narrowed region of the blood vessel 50. This can be accomplished by pulling on the handle assembly 20. In doing so, the incising elements 36 engage the atherosclerotic material 54 and create longitudinal incisions 56 therein. As shown in FIGS. 6 and 7, the outer surface area of the arcuate shaped struts 34A and 34B, which is adjacent to the incising element 36, is configured to ride along a surface of the atherosclerotic material 54, thereby limiting the depth of the incisions 56 and preventing the incising members 36 from cutting the walls of the blood vessel 50. The expandable portion 32 can be moved any distance along the guide wire 52 to create incisions 56 having any desired length. After the incisions 56 are made in the atherosclerotic material 54, the catheter device 10 can be returned to the first operating mode (shown in FIGS. 1 through 4) by moving the control member 25 to the forward position. In doing so, the expandable portion 32 returns to the closed position. The protective sheath 42 can be slid over the expandable portion 32 and the catheter tube 30 may be removed from the blood vessel 50.

Alternatively, the catheter device 10 can be used to create additional incisions 56 in the atherosclerotic material 54. For example, after the catheter device 10 has been returned to the first operating mode, the expandable portion 32 can be relocated within the narrowed region of the blood vessel 50. The catheter tube 30 can then be rotated within the blood vessel 50 by rotating the handle assembly 20 so as to align the incising elements 36 with other portions of the atherosclerotic material 54. The previous steps can then be repeated any number of times to make multiple passes through the narrowed region of the blood vessel 50 and create additional incisions in the atherosclerotic material 54.

Thus, it should be appreciated that the illustrated catheter device 10 is advantageous in many respects. In one example, the second diameter D2 of the expandable portion 32 can be selectively controlled by operation of the handle assembly 20 or by sliding movement of the protective sheath 42. This enables the catheter device 10 to be adapted for use in blood vessels 50 of different sizes or varying diameters. In another example, the illustrated catheter device 10 can apply varying magnitudes of radial forces to the atherosclerotic material 54 by controlling the amount of force being applied to the control member 25 on the handle assembly 20. This enables the catheter device 10 to generate sufficient radial force to create incisions 56 in atherosclerotic material 54 while reducing the potential for tearing the walls of the blood vessel 50. In yet another example, the catheter device 10 can be used to make any number of passes during a single procedure to make multiple incisions 56 in atherosclerotic material 54 of varying lengths and shapes.

Figure 8:
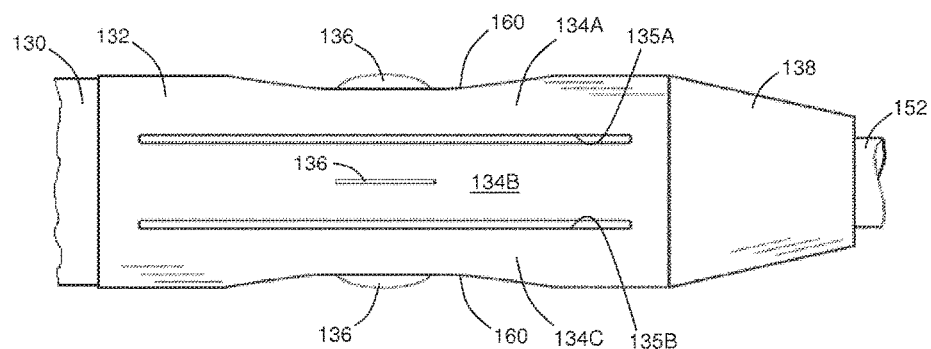
FIG. 8 is an enlarged side view of a catheter tube having an expandable incising portion, in accordance with a second embodiment of this invention.
Figure 9:
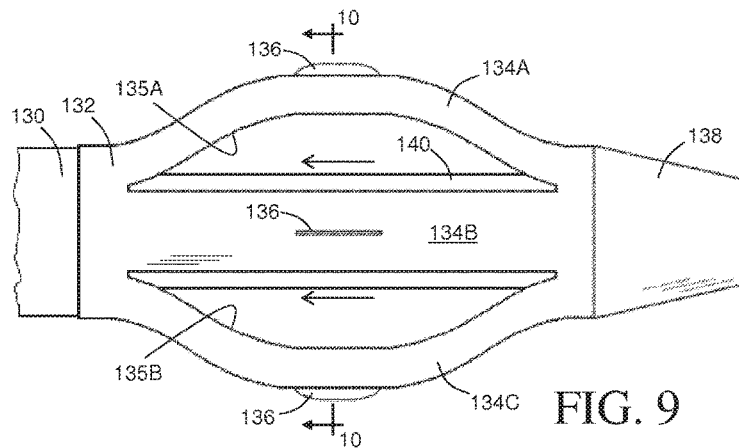
FIG. 9 is a side view of the catheter tube shown in FIG. 8 illustrating the expandable incising portion in an opened position.
Figure 10:
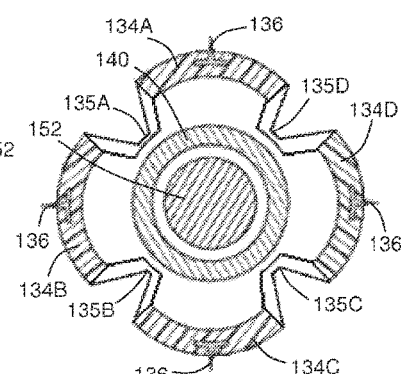
FIG. 10 is a cross-sectional end view of the expandable incising portion taken along section line 10-10 shown in FIG. 9.

Referring now to FIGS. 8 through 10, there is illustrated a catheter tube 130 having an expandable portion 132, in accordance with a second embodiment of this invention. The catheter tube 130 and the expandable portion 132 may include any structural features as described and illustrated above in the previous embodiment, although such is not required. Similar features have been numbered with common reference numerals but have been increased by 100 (i.e., 110, 120, 130, etc.). It should be appreciated that similar features are structured similarly, operate similarly, and/or have the same function unless otherwise indicated by the drawings or this specification.

For example, the catheter tube 130 may extend from a handle assembly (not shown) as described above in the first embodiment. The expandable portion 132 is provided on a distal end of the catheter tube 130 and may include a tip member 138. The catheter tube 130 may also include an inner sleeve 140 and a protective sheath (not shown), which is also described above in the first embodiment.

In the illustrated embodiment, however, the expandable portion 132 includes four struts 134A, 134B, 134C, and 134D that are respectively separated by four longitudinally extending slits 135A, 135B, 135C, and 135D. The illustrated struts 134A, 134B, 134C, and 134D each include an incising element 136, although such is not required. It should be appreciated that the expandable portion 132 may have any number or configuration of struts and incising elements as desired.

As shown in FIG. 8, the illustrated expandable portion 132 further includes recessed portions 160 that respectively extend into the outer surfaces of the struts 134A, 134B, 134C, and 134D. For example, the struts 134A, 134B, 134C, and 134D can be slightly bowed inwardly toward the inner sleeve 140 when in the closed position or, alternatively, may have a reduced thickness along a central portion thereof to create the recessed portions 160. The illustrated incising elements 136 are respectively disposed within the recessed portions 160. Thus, when the catheter tube 130 is inserted into a blood vessel, as described above, the recessed portions 160 help to prevent the incising elements 136 from coming into contact with inner walls of the blood vessel. On the other hand, when the expandable portion 132 is expanded to an opened position, as explained below, the incising elements 136 become exposed from the recessed portions 160. It should be appreciated that the recessed portions 160 can eliminate or reduce the need for the protective sheath (not shown). The guide wire 152 may extend through the entire device.

The expandable portion 132 can be operated between a closed position (shown in FIG. 8) and an opened position (shown in FIGS. 9 and 10) by selective movement of the inner sleeve 140 relative to the catheter tube 130, as described above in the first embodiment. Alternatively (or in addition), the struts 134A, 134B, 134C, and 134D can be biased in the opened position. In such an embodiment, the protective sheath (not shown) can be used to effect movement of the expandable portion 132 between the closed position and the opened position.

Figure 11:
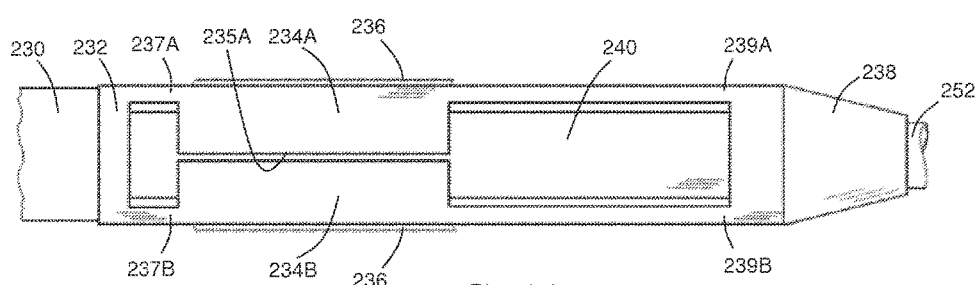
FIG. 11 is an enlarged side view of a catheter tube having an expandable incising portion, in accordance with a third embodiment of this invention.
Figure 12:
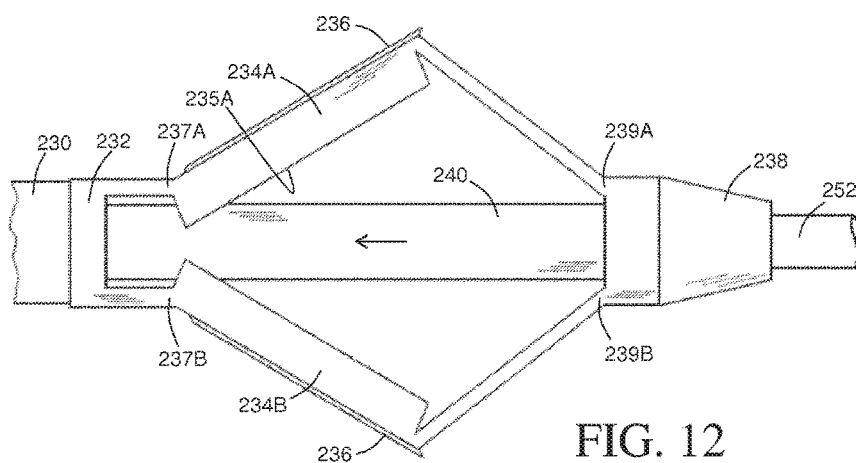
FIG. 12 is a side view of the catheter tube shown in FIG. 11 illustrating the expandable incising portion in an opened position.
Figure 13:
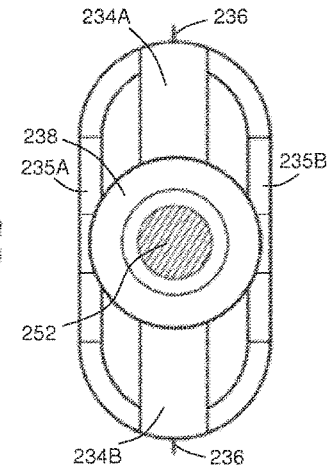
FIG. 13 is an end view of the catheter tube as shown in FIG. 12.

Referring now to FIGS. 11 through 13, there is illustrated a catheter tube 230 having an expandable portion 232, in accordance with a third embodiment of this invention. The catheter tube 230 and the expandable portion 232 may include any structural features as described and illustrated above in the previous embodiments, although such is not required. Similar features have been numbered with common reference numerals but have been increased by 200 (i.e., 210, 220, 230, etc.). It should be appreciated that similar features are structured similarly, operate similarly, and/or have the same function unless otherwise indicated by the drawings or this specification.

For example, the catheter tube 230 may extend from a handle assembly (not shown) as described above in the first embodiment. The expandable portion 232 is provided on a distal end of the catheter tube 230 and includes a pair of struts 234A and 234B that are separated by a pair of longitudinally extending slits 235A and 235B. The catheter tube 230 may also include a tip member 238, an inner sleeve 240, and a protective sheath (not shown), which is described above in the first embodiment. The guide wire 252 may extend through the entire device.

In the illustrated embodiment, however, the expandable portion 232 includes a first pair of weakened regions 237A, 237B and a second pair of weakened regions 239A, 239B that are respectively located at opposite ends of the struts 234A and 234B. The illustrated weakened regions 237A, 237B and 239A, 239B are formed by enlarged apertures that extend through side walls of the expandable portion 232 that function as hinges. The weakened regions 237A, 237B and 239A, 239B may help reduce the amount of bending stress in the side walls of the expandable portion 232 when the struts 234A and 234B are moved to an opened position. The struts 234A and 234B may include any number or configuration of weakened regions. Further, it should be appreciated that any of the other embodiments in this disclosure may also include weakened regions 237A, 237B and 239A, 239B.

The illustrated struts 234A and 234B remain generally flat along respective lengths thereof in both a closed position (shown in FIG. 11) and an opened position (shown in FIGS. 12 and 13) so as to form an apex, although such a configuration is not required. The incising elements 236 are provided along the generally flat portion of the respective struts 234A and 234B. As such, the incising elements 236 may also function as stiffening members for increasing the strength of the struts 234A and 234B. Further, this configuration can reduce the amount of stress in the connection between the incising elements 236 and the struts 234A and 234B, which may otherwise be caused by bowing of the struts 234A and 234B.

As shown in FIG. 12, end portions of the incising elements 236 may extend beyond the apex that is formed by each of the respective struts 234A and 234B. This configuration can increase the effective height of the incising elements 236 when the expandable portion 232 is in the opened position. As such, the incising elements 236 may have a reduced height when the expandable portion 232 is in the closed position, which may eliminate the need for the protective sheath (not shown).

The expandable portion 232 can be operated between the closed position and the opened position by selective movement of the inner sleeve 240 relative to the catheter tube 230, as described above in the first embodiment. Alternatively (or in addition), the struts 234A and 234B can be biased in the opened position. In such an embodiment, the protective sheath (not shown) can be used to effect movement of the expandable portion 232 between the closed position and the opened position.

Figure 14:
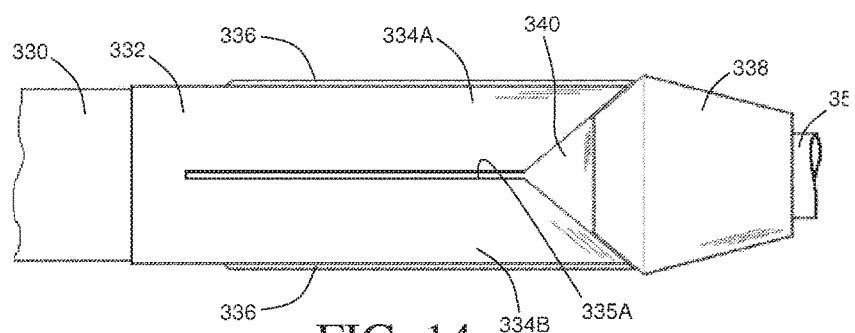
FIG. 14 is an enlarged side view of a catheter tube having an expandable incising portion, in accordance with a fourth embodiment of this invention.
Figure 15:
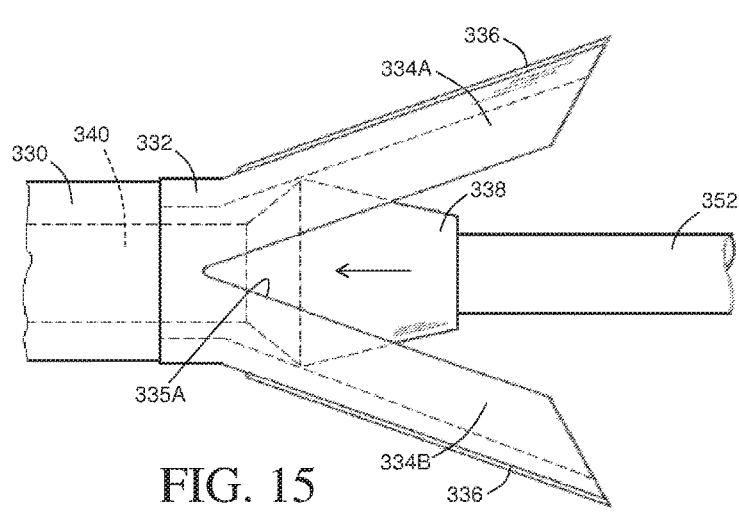
FIG. 15 is a side view of the catheter tube shown in FIG. 14 illustrating the expandable incising portion in an opened position.
Figure 16:
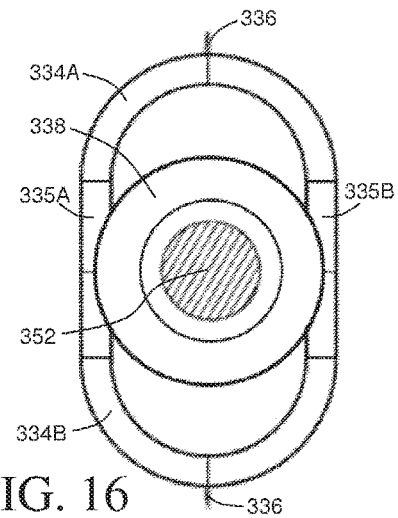
FIG. 16 is an end view of the catheter tube as shown in FIG. 15.

Referring now to FIGS. 14 through 16, there is illustrated a catheter tube 330 having an expandable portion 332, in accordance with a fourth embodiment of this invention. The catheter tube 330 and the expandable portion 332 may include any structural features as described and illustrated above in the previous embodiments, although such is not required. Similar features have been numbered with common reference numerals but have been increased by 300 (i.e., 310, 320, 330, etc.). It should be appreciated that similar features are structured similarly, operate similarly, and/or have the same function unless otherwise indicated by the drawings or this specification.

For example, the catheter tube 330 may extend from a handle assembly (not shown) as described above in the first embodiment. The expandable portion 332 is provided on a distal end of the catheter tube 330 and may include a tip member 338. The catheter tube 330 may also include an inner sleeve 340 that is attached to the tip member 338 and a protective sheath (not shown), which is also described above in the first embodiment. The guide wire 352 may extend through the entire device.

In the illustrated embodiment, however, the expandable portion 332 includes a pair of struts 334A and 334B that are supported thereon in a cantilevered manner (i.e., not attached to one another or to the tip member 338 at their distal ends), the purpose of which will be explained below. The struts 334A and 334B are separated by a pair of longitudinally extending slits 335A and 335B that extend from the end of the expandable portion 332. A pair of incising elements 336 is respectively provided along outer surfaces of the struts 334A and 334B. It should be appreciated, however, that the expandable portion 332 may have any number or configuration of struts and incising elements as desired.

As shown in FIGS. 15 and 16, the illustrated struts 334A and 334B are supported on the expandable portion 332 so that they can be splayed open in a Y-shaped configuration. For example, the struts 334A and 334B can be splayed open by drawing the inner sleeve 340 within the catheter tube 330, as described above in the first embodiment. In doing so, the tip member 338 slides along the inner surfaces of the struts 334A and 334B and pivots them outwardly. Alternatively (or in addition), the struts 334A and 334B can be biased in the splayed open position. In such an embodiment, the protective sheath (not shown) can be used to effect movement of the expandable portion 332 between a closed position and the splayed open position.

The struts 334A and 334B remain generally flat along their respective lengths in both a closed position (shown in FIG. 14) and the splayed open position, although such is not required. As such, the incising elements 336 may also function as stiffening members for increasing the strength of the struts 334A and 334B. Further, this configuration can reduce the amount of stress in the connection between the incising elements 336 and the struts 334A and 334B, which may otherwise be caused by bowing of the struts 334A and 334B.

As shown in FIG. 15, end portions of the incising elements 336 may extend beyond the distal ends of the respective struts 334A and 334B. This configuration can increase the effective height of the incising elements 336 when the expandable portion 332 is in the splayed open position. As such, the incising elements 336 may have a reduced height when the expandable portion 332 is in the closed position, which may eliminate the need for the protective sheath (not shown).

The principle and mode of operation of this invention have been explained and illustrated in its preferred embodiments. However, it must be understood that this invention may be practiced otherwise than as specifically explained and illustrated without departing from its spirit or scope.

What is claimed is:

1. An intravascular catheter device for the treatment of atherosclerotic material located within a blood vessel, said intravascular catheter device comprising:
   a flexible catheter tube;
   an expandable portion secured to a distal end of said catheter tube and comprising a plurality of struts each having an outer surface, the expandable portion being operable between a collapsed position, wherein the expandable portion has a first diameter, and an expanded position, wherein the expandable portion has a second diameter that is larger than the first diameter;

an inner sleeve disposed within the catheter tube wherein said inner sleeve is configured for sliding movement within the catheter tube to effectuate movement of said expandable portion between said collapsed position and said expanded position, and wherein said inner sleeve is configured to accommodate a guide wire; and an incising element provided at, and extending from, the outer surface of at least one of the struts, the incising element having a sharpened edge;

wherein said incising element is configured to extend along a longitudinal axis of the expandable portion when the expandable portion is in the collapsed position and is configured to incise atherosclerotic material located in the blood vessel and create microparticles of the atherosclerotic material for reabsorption into the blood vessel when the expandable portion is located in the expanded position.

2. The intravascular catheter device of claim 1 wherein: the sharpened edge is located along an upper edge of the incising element and extends along the outer surface of the strut.

3. The intravascular catheter device of claim 2 wherein: the incising element extends along a longitudinal axis of the blood vessel.

4. The intravascular catheter device of claim 2 wherein: the incising element extends along a midline of the strut; and
the incising element extends outward from the outer surface of the strut.

5. The intravascular catheter device of claim 4 wherein: the incising element extends along a proximal half of the at least one strut.

6. The intravascular catheter device of claim 1 further comprising:
a tip member attached to the inner sleeve and the expandable portion to effectuate movement of the struts between the collapsed position and the expanded position when the tip member is extended or retracted relative to the catheter tube by way of the inner sleeve.

7. The intravascular catheter device of claim 6 further comprising:
a handle assembly secured to a proximal end of the catheter tube; and
a control member that is moveably supported on the handle assembly and in communication with the inner sleeve, wherein said control member is configured to control movement of the expandable portion between the collapsed and the expanded position by way of the inner sleeve.

8. The intravascular catheter device of claim 1 wherein: the incising element extends along a longitudinal axis of the expandable portion when the expandable portion is in the expanded position.

9. The intravascular catheter device of claim 1 further comprising:
a sheath supported for sliding movement between a retracted position where said incising elements are exposed, and an advanced position where said sheath is disposed about said expandable portion such that material deposited on said incising element is captured, and wherein the sheath, and any captured material deposits, is adapted to be removed from the blood vessel.

10. The intravascular catheter device of claim 1 wherein: the incising elements are configured to create incisions which break the surface tension in the atherosclerotic material and create luminal gain.

11. An intravascular catheter device for the treatment of atherosclerotic material located within a blood vessel, said intravascular catheter device comprising:
a handle assembly;
a flexible catheter tube having a proximal end secured to said handle assembly;
an expandable portion secured to a distal end of said catheter tube comprising a plurality of struts each defining an outward facing surface and being operable between a collapsed position, wherein the expandable portion has a first diameter, and an expanded position, wherein the expandable portion has a second diameter that is larger than the first diameter;
an incising element extending along a midline of, and outwardly from, the outward facing surface of at least one of the struts;
a sharpened edge positioned along an upper edge of said incising element, wherein said sharpened edge extends along a longitudinal axis of the expandable portion when the expandable portion is in the collapsed position, and wherein said sharpened edge is configured to incise the atherosclerotic material when the expandable portion is placed in the expanded position; and
a flexible inner sleeve disposed within the catheter tube and supported for sliding movement within the catheter tube to cause movement of said expandable portion between said collapsed position and said expanded position;
wherein said sharpened edge is configured to generate microparticles of the atherosclerotic material when incising said atherosclerotic material.

12. The intravascular catheter device of claim 11 wherein: the incising element extends along a longitudinal axis of the expandable portion when the expandable portion is in the expanded position.

13. The intravascular catheter device of claim 11 further comprising:
a tip member attached to the inner sleeve and the expandable portion so as to move the struts between the collapsed position and the expanded position when the tip member is extended or retracted relative to the catheter tube, wherein said tip member and said flexible inner sleeve are configured to accommodate the guide wire; and
a control member located on the handle assembly and configured to facilitate the sliding movement of the inner sleeve.

14. The intravascular catheter device of claim 13 further comprising:
a sheath supported for sliding movement along an outer surface of the catheter tube, the sheath being operable between an opened position where said incising members are exposed, and a closed position where said sheath covers said expandable portion, wherein said sheath is configured to trap any material deposited on said incising element when said sheath is placed in the closed position.

15. The intravascular catheter device of claim 11 wherein: said sharpened edge extends outwardly from the outer surface of the strut.

16. The intravascular catheter device of claim 11 wherein: the struts are biased in the expanded position.

17. The intravascular catheter device of claim 11 wherein:
the incising elements are configured to create incisions which break the surface tension in the atherosclerotic material and create luminal gain.

18. A method for the treatment of atherosclerotic material at a zone of attention located within a blood vessel comprising the steps of:
providing an intravascular device comprising:
- a flexible catheter tube;
- an expandable portion secured to a distal end of said catheter tube comprising a plurality of struts, each defining an outward facing surface and being operable between a collapsed position wherein the expandable portion has a first diameter and an expanded position wherein the expandable portion has a second diameter that is larger than the first diameter;
- a flexible inner sleeve disposed within the catheter tube and supported for sliding movement within the catheter tube atop a guide wire;
- an incising element provided on, and extending outwardly from, the outward facing surface of at least one of the struts and extending longitudinally along at least a portion thereof; and
- a sharpened edge located along an upper edge thereof for incising and generating microparticles of atherosclerotic material, said sharpened edge extending along a longitudinal axis of the expandable portion when the expandable portion is in the closed position;

locating the intravascular device at the zone of attention;
placing the expandable portion in the expanded position by sliding movement of the flexible inner sleeve in a first direction;
manipulating the intravascular device along the zone of attention so as to incise the atherosclerotic material and generate microparticles of the atherosclerotic material for absorption into the blood vessel; and
placing the expandable portion in the collapsed position by sliding movement of the flexible inner sleeve in a second direction.

19. The method of claim 18 further comprising the steps of:
providing a sheath on the intravascular device, wherein the sheath is configured to be operable between an open position where the incising members are exposed, and a closed position where the sheath covers the expandable portion;
placing the expandable portion within the vascular system of a patient;
placing the sheath in the open position;
placing the protective sheath in the closed position so as to trap any material deposited on the incising elements; and
removing the expandable portion from the patient's vascular system.

20. The method of claim 18 wherein:
the sharpened edge is configured to create incisions which break the surface tension in the atherosclerotic material and create luminal gain.

* * * * *